United States Patent [19]
Gatturna et al.

[11] Patent Number: 5,554,171
[45] Date of Patent: *Sep. 10, 1996

[54] SUTURE ANCHOR

[75] Inventors: Roland F. Gatturna, Walpole; James E. Nicholson, Lincoln; James O'Leary, Medford, all of Mass.

[73] Assignee: Mitek Surgical Products, Inc., Westwood, Mass.

[*] Notice: The term of this patent shall not extend beyond the expiration date of Pat. No. 5,898,156.

[21] Appl. No.: 327,584

[22] Filed: Oct. 24, 1994

Related U.S. Application Data

[63] Continuation of Ser. No. 981,011, Nov. 24, 1992, Pat. No. 5,358,511, which is a continuation of Ser. No. 853,261, Mar. 18, 1992, Pat. No. 5,192,303, which is a continuation of Ser. No. 711,145, Jun. 6, 1991, abandoned, which is a continuation of Ser. No. 439,452, Nov. 20, 1989, Pat. No. 5,046,513, which is a continuation of Ser. No. 51,367, May 18, 1987, Pat. No. 4,898,156.

[51] Int. Cl.$^6$ ................................................. A61B 17/04
[52] U.S. Cl. ........................................................ 606/232
[58] Field of Search ....................................... 606/72, 232

[56]   References Cited
   U.S. PATENT DOCUMENTS

| 4,669,473 | 6/1987 | Richards et al. | 606/232 |
| 4,738,255 | 4/1988 | Goble | 606/232 |
| 4,741,330 | 5/1988 | Hayhurst | 606/232 |

*Primary Examiner*—Gary Jackson
*Attorney, Agent, or Firm*—Pandiscio & Pandiscio

[57]   ABSTRACT

A suture anchor for anchoring one end of a conventional suture to bone comprising a coupling member, at least one barb made of a resilient elastic material projecting form said coupling member, and means for attaching one end of a suture to said suture anchor. The coupling member and the at least one barb and adapted to securely anchor one end of the suture in bone when the suture is attached to the attachment means so that the other end of the suture extending outside the bone can be used to attach objects to the bone. A novel application tool is also provided.

4 Claims, 8 Drawing Sheets

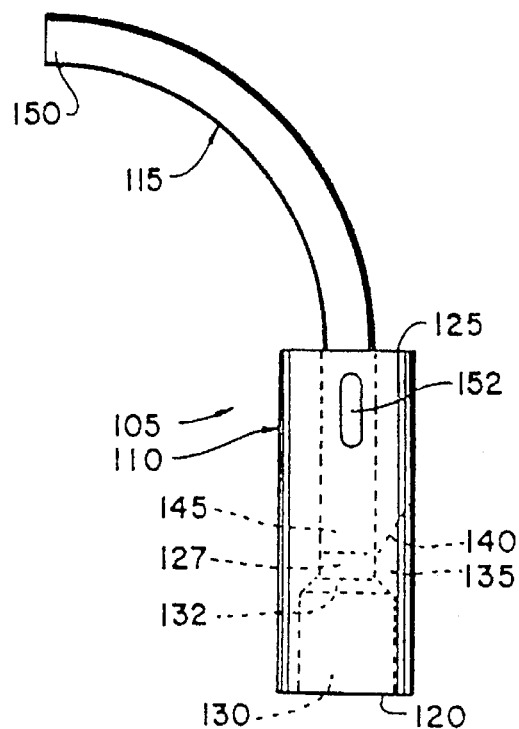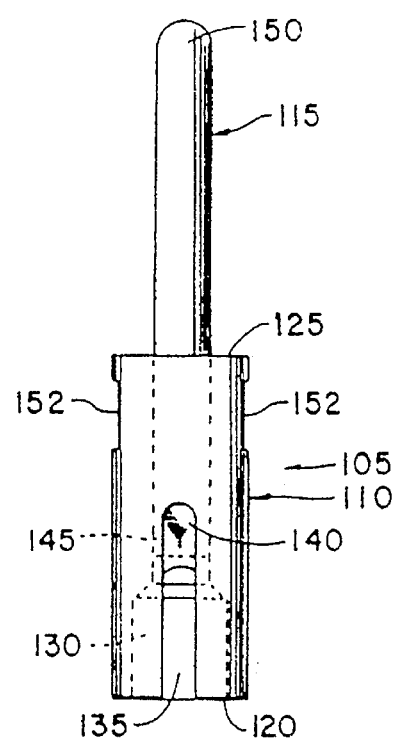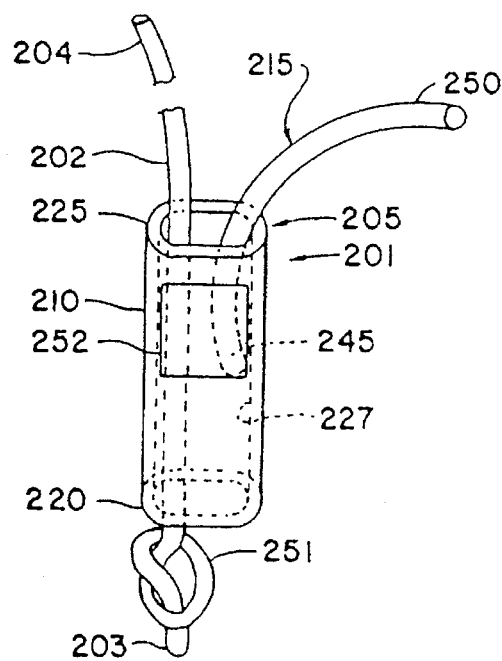

SUTURE ANCHOR

This is a continuation of U.S. patent application Ser. No. 07/981,011, filed Nov. 24, 1992, now U.S. Pat. No. 5,358, 511 by Roland F. Gatturna et al. for Suture Anchor, which is itself a continuation of U.S. patent application Ser. No. 07/853,261, filed Mar. 18, 1992, now U.S. Pat. No. 5,192, 303 by Roland F. Gatturna et al. for Suture Anchor, which is itself a continuation of U.S. patent application Ser. No. 07/711,145, filed Jun. 06, 1991, now abandoned by Roland F. Gatturna et al. for Suture Anchor, which is itself a continuation of U.S. patent application Ser. No. 07/439,452, filed Nov. 20, 1989, now U.S. Pat. No. 5,046,513 by Roland F. Gatturna et al. for Method For Anchoring Suture To Bone (As Amended), which is itself a continuation of U.S. patent application Ser. No. 07/051,367, filed May 18, 1987, now U.S. Pat. No. 4,898,156 by Roland F. Gatturna et al. for Suture Anchor.

FIELD OF THE INVENTION

This invention relates to surgical devices in general, and more particularly to devices of the sort adapted to attach objects to bone.

BACKGROUND OF THE INVENTION

Numerous devices are currently available to attach objects to bone. More specifically, screws, staples, cement and sutures have all been used to attach soft tissue (e.g. ligaments, tendons, muscles, etc.), bone and inanimate objects (e.g. prostheses) to bone. Unfortunately, all of the foregoing attachment devices tend to suffer from one or more serious disadvantages.

Screws suffer from the disadvantage that they tend to loosen with time, thereby requiring a second operation to remove the loosened screw. In addition, when the screws are set in bone, the heads of the screws frequently protrude above the surface of the bone in which they are set, thereby presenting an abrasive surface which may create wear problems with surrounding tissue. Also, properly fastening the screws into bone can be time-consuming, since a pilot hole must normally be drilled into the bone and then, depending on the bone structure, the bone may also have to be tapped to accept the screw. Furthermore, once the pilot hole has been drilled, the position of the screw is then determined so that it is impossible to thereafter alter the position of the screw or to adjust the degree of tension being applied to the object which is being attached to the bone without drilling a new hole. Also, once a hole has been made in the bone it may be impossible to relocate the hole in a small distance away from its original position due to the disruption of the bone structure created by the initial hole. Finally, the nature of a screw attachment tends to require a flat attachment geometry; the pilot hole must generally be located on a relatively flat section of the bone, and toothed washers must frequently be used in conjunction with the screws to fasten the desired objects to the target bone. As a result of these constraints, it may be necessary to locate the attachment point at a less than optimal position.

Staples suffer from their own set of disadvantages. More particularly, bone staples must frequently be removed after they have been in position for some time, thereby necessitating a second operation. In addition, staples must generally be positioned so as to maximize their holding power in the bone; such positioning may conflict with the otherwise-optimal position for attachment of the objects to bone. Staples have also been known to crack the bone during deployment, or to accidentally transect the object (e.g. soft tissue) being attached to the bone, since it tends to be difficult to precisely control the extent of the staple's penetration into the bone. Finally, as is the case with screws, once the staple has been set into the bone the position of the staple is then effectively determined, thereby making it impossible to thereafter adjust the position of the staple or to adjust the degree of tension being applied to the object which is being attached to the bone without setting a new staple.

Cement can be a better solution than screws or staples where an object is being attached to the INTERIOR portion of the bone, e.g. as in the case of a total hip replacement, but it is generally unsatisfactory where an object must be attached to the EXTERIOR surface of the bone. The use of cement can also raise problems relating to setting time, part immobilization during setting time, and substance compatibility with body tissues.

The use of sutures to attach objects to bone is accompanied by a different, but no less troublesome, set of problems. Sutures generally require that holes be drilled in the bone prior to suturing so that the sutures can be passed through the holes in the course of attaching objects to the bone. Drilling these suture-receiving holes in the bone can be time-consuming; in addition, since the sutures which are used to attach objects to the bone are generally quite thin (e.g. 0.020 inches) and since the load imposed on the sutures is generally quite sizable, the sutures have been known to pull completely through the bone, thereby failing as an attachment device and possibly seriously damaging the bone as well.

OBJECTS OF THE INVENTION

Accordingly, one of the objects of the present invention is to provide improved apparatus for attaching objects to bone which avoids the aforementioned problems associated with prior art devices.

Another object of the present invention is to provide a novel suture anchor for anchoring one end of a piece of conventional suture in bone and leaving the other end of the piece of suture residing free outside the bone so that the free end of the suture can then be used to attach the desired object (e.g. a ligament or prosthesis) to the bone.

Still another object of the present invention is to provide a novel suture anchor for anchoring one end of a piece of conventional suture in bone which is made out of biocompatible materials which eliminate, or at least minimize, any problem of rejection by surrounding tissue.

Yet another object of the present invention is to provide a novel suture anchor for anchoring one end of a piece of conventional suture in bone which will attach itself securely to the target bone and which has virtually no tendency to migrate from its deployment site.

And another object of the present invention is to provide a novel suture anchor for anchoring one end of a piece of conventional suture in bone which is low in cost, simple to manufacture, and reliable in use.

Yet another object of the present invention is to provide a novel method for attaching objects to bone which utilizes the novel suture anchor now disclosed.

And another object of the present invention is to provide a novel suture and suture anchor assembly comprising a suture and a suture anchor for anchoring one end of the piece of suture in bone and leaving the other end of the suture residing free outside the bone so that the free end of the suture can be used to attach objects to the bone.

Yet another object of the present invention is to provide a novel method for attaching objects to bone which utilizes the novel suture and suture anchor assembly now disclosed.

Still another object of the present invention is to provide a novel post and post anchor assembly for anchoring one end of the post in bone and leaving the other end of the post residing free outside the bone so that the free end of the post can be used to attach objects to the bone.

Yet another object of the present invention is to provide a novel method for attaching objects to bone which utilizes the novel post and post anchor assembly now disclosed.

Still another object of the present invention is to provide a novel prosthesis and prosthesis anchor assembly comprising a prosthesis and a prosthesis anchor for anchoring one end of the prosthesis in bone.

And another object of the present invention is to provide a novel method for attaching prosthesis to bone which utilizes the novel prosthesis and prosthesis anchor assembly now disclosed.

Still another object of the present invention is to provide a novel installation tool for deploying the novel suture anchor in bone.

SUMMARY OF THE INVENTION

These and other objects of the present invention are achieved by a novel suture anchor which comprises a coupling member and at least one barb. The coupling member comprises a relatively rigid member which is substantially straight along a first axis. The barb comprises a relatively strong piece of wire having a first end and a second end and which is significantly curved in its unrestrained state but which is capable of being elastically deformed to a substantially straight length when desired. The barb is attached to the coupling member adjacent the barb's first end, whereby (a) when the barb is in its curved, unrestrained state the second end of the barb extends radially outward from, and is significantly displaced from, the first axis of the coupling member, and (b) when the barb has been elastically deformed to a substantially straight length, the second end of the barb will be aligned with both the first end of the barb and the first axis of the coupling member. The coupling member also includes attachment means for attaching a suture to the suture anchor.

The foregoing suture anchor is used to attach objects to bone in the following manner. The suture anchor is prepared for use by loading it into an installation tool so that the coupling member is in a leading position with the coupling member's attachment means remaining exposed and with the second end of the barb being elastically deformed backwards so that the barb extends substantially straight, i.e., so that the second end of the barb is aligned with both the first end of the barb and the first axis of the coupling member. Next, a conventional suture of the sort having a first end and a second end is attached to the coupling member's attachment means so that the suture is joined to the coupling member at the suture's first end and the suture's second end is left free. The suture anchor and its attached suture together form a suture and suture anchor assembly. (It is also to be appreciated that the suture and suture anchor assembly could be preassembled prior to loading the suture anchor into the installation tool, as will hereinafter be described in detail.) Either before or after the suture anchor has been loaded into the installation tool and the suture attached to the suture anchor, but in any case before the suture and suture anchor assembly is attached to the target bone, a hole is drilled into the bone. Once the foregoing loading, attachment and drilling operations have been completed, the suture and suture anchor assembly is ready to be attached to the bone. This is achieved by using the installation tool to inject the suture anchor (and its attached first end of the suture) into the hole formed in the bone; as the suture anchor is injected into the hole, the suture anchor's barb is released from the constraining environment of the installation tool and immediately attempts to return to its unconstrained, curved state. By appropriately sizing the suture anchor and the hole formed in the bone, the barb will be permitted to return only part way back to its original unconstrained curved state before it engages the side wall of the bone's hole and locks the suture anchor (and hence the first end of the suture) securely in place in the bone. The wire barb then effectively prevents the suture anchor from being pulled out of the bone when a pulling force is applied to the second, free end of the suture. The second, free end of the suture may then be used in ways well known in the art to attach objects to the bone holding the suture anchor.

Alternative embodiments (and methods of using the same) are also disclosed wherein the suture is replaced by a post, or by one end of a prosthesis itself; with these alternative embodiments, the anchor serves to anchor one end of the post or one end of the prosthesis to the bone.

A novel installation tool for deploying the novel suture anchor in bone is also disclosed.

BRIEF DESCRIPTION OF THE DRAWINGS

Still other objects and features of the present invention will be more fully disclosed or rendered obvious in the following detailed description of the invention, which is to be considered together with the accompanying drawings wherein like numbers refer to like parts and further wherein;

FIG. 8 is a side view in elevation showing another suture anchor formed in accordance with the present invention;

FIG. 9 is a side view in elevation showing another side of the suture anchor of FIG. 8;

FIG. 10 is a perspective view showing another suture and suture anchor assembly formed in accordance with the present invention;

DETAILED DESCRIPTION OF THE INVENTION

Figure 1:
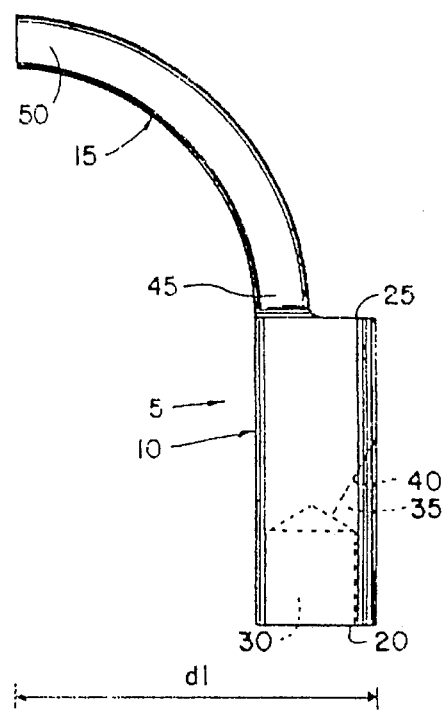
FIG. 1 is a side view in elevation showing one side of a suture anchor formed in accordance with the present invention.
Figure 2:
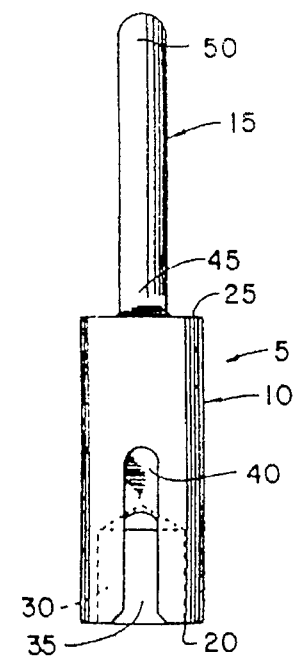
FIG. 2 is a side view in elevation showing another side of the suture anchor of FIG. 1.

Looking first at FIGS. 1 and 2, there is shown a suture anchor 5 which generally comprises a coupling member 10 and a barb 15.

Coupling member 10 comprises a piece of nickel titanium alloy having a first end 20 and a second end 25. Coupling member 10 has a blind hole 30 opening on its first end 20. A side slot 35 opens on the coupling member's first end 20 and communicates with its blind hole 30. Side slot 35 terminates in an inclined surface 40 intermediate the length of coupling member 10. Coupling member 10 has a length of approximately 0.156 inches and a width of approximately 0.062 inches, blind hole 30 has a diameter of approximately 0.042 inches and a depth of approximately 0.050 inches, and side slot 35 has a length of approximately 0.093 inches (as measured between the coupling member's first end 20 and the point where inclined surface 40 opens on the exterior of coupling member 10) and a width of approximately 0.020 inches.

Barb 15 comprises a curved length of nickel titanium alloy having a first end 45 and a second end 50. The barb's first end 45 is attached to the coupling member's second end 25 so that barb 15 extends upward away from the coupling member. Barb 15 is preferably formed integral with coupling member 10, e.g. by machining suture anchor 5 out of a single piece of nickel titanium alloy. Barb 15 has a width of approximately 0.026 inches and, in its unrestrained state, comprises an arc of approximately 90 degrees of a loop approximately 0.250 inches in diameter (when measured to the inside edge of the loop). Barb 15 is capable of being elastically deformed to a substantially straight length when desired (e.g. so that the barb's second end 50 is aligned with its first end 45, as well as with the coupling member's first end 20 and its second end 25).

Preferably coupling member 10 and barb 15 are formed out of a nickel titanium alloy such as Nitinol (R) or Tinel (R) sold commercially by RayChem, or Sentinol (R) sold commercially by GAC International, Inc. However, equivalent nickel titanium materials, as well as equivalent non-nickel titanium materials, may also be used.

Figure 3:
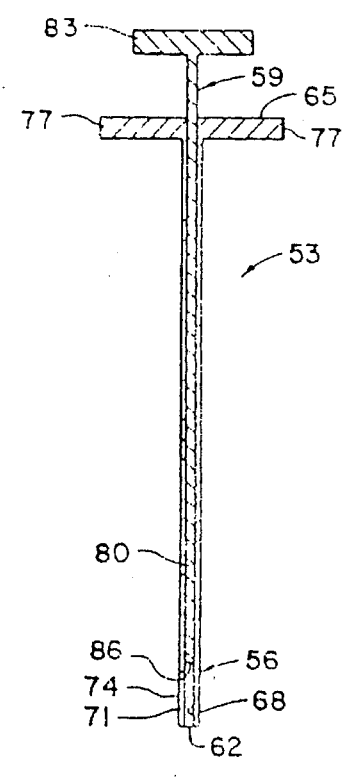
FIG. 3 is a side view in elevation, in section, showing an installation tool which may be used to install the new suture anchor in bone.

Looking next at FIG. 3, the suture anchor is intended to be utilized in conjunction with an installation tool 53. Tool 53 generally comprises a hollow sheath 56 and a plunger 59. Sheath 56 terminates in a flat annular surface 62 at its front end and a flat annular surface 65 at its rear end. Surfaces 62 and 65 are disposed at an angle substantially perpendicular to the longitudinal axis of sheath 56. Sheath 56 has an axial bore 68 extending between its front surface 62 and its rear surface 65, and a straight slot 71 extending rearwardly from the tool's front surface 62 and terminating in a rear surface 74. Sheath 56 also includes a pair of rigid finger grips 77 which extend radially outward from the sheath near its rear surface 65. Sheath 56 preferably has an outer diameter (i.e., forward of finger grips 77) of approximately 0.095 inches, an inner diameter of approximately 0.071 inches, and a length of approximately 5 inches. The sheath's straight slot 71 preferably has a length of approximately 0.187 inches and a width (when measured in the circumferential direction of sheath 56) of approximately 0.030 inches.

Plunger 59 is a one-piece unit and includes a body section 80 and a head section 83. Body section 80 has a round cross-section and terminates in a front surface 86. Plunger 59 is sized so that its body section 80 will make a close sliding fit within bore 68 of sheath 56, and so that its leading tip 86 will protrude from the front end of the sheath a short distance when the plunger's head section 83 is in engagement with the sheath's rear surface 65. Plunger 59 preferably has a diameter of approximately 0.058 inches forward of head section 83, and a length of approximately 5 inches.

Figure 4A:
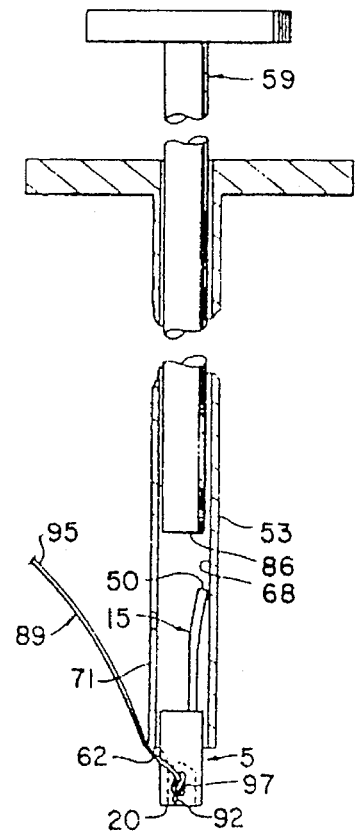
FIG. 4A is a side view in elevation, partially in section, showing a suture anchor assembly partially loaded into an installation tool and just after attachment of the suture to the suture anchor.
Figure 4B:
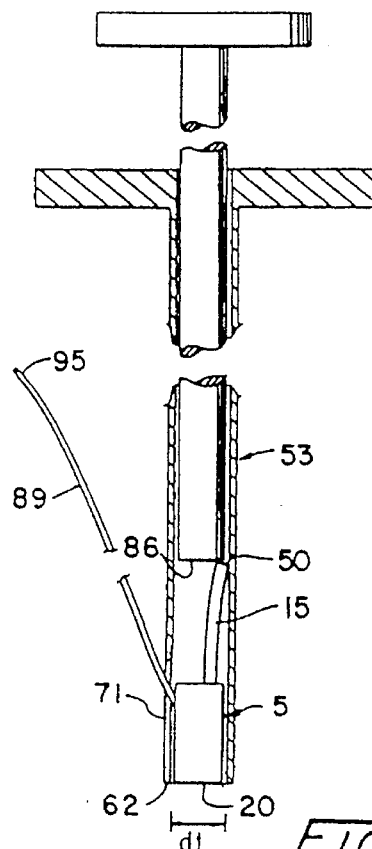
FIG. 4B is a side view in elevation, partially in section, showing a suture and suture anchor assembly fully loaded into an installation tool, but prior to deployment of the suture and suture anchor assembly into bone.
Figure 5:
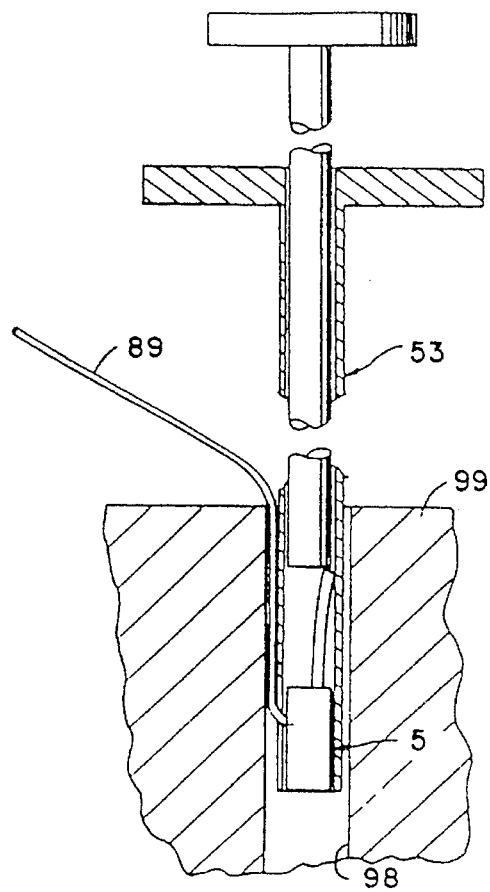
FIG. 5 is a side view in elevation, partially in section, showing a suture and suture anchor assembly loaded into an installation tool, with the installation tool having been inserted into a hole formed in a bone but with the suture and suture anchor assembly not yet having been ejected out of the installation tool and into the hole formed in the bone.

Installation tool 53 is adapted to receive suture anchor 5 in the manner shown in FIG. 4A, i.e., the suture anchor is intended to be forced part way into the interior bore 68 of tool 53, barbed end first, so that the second end 50 of the barb is located adjacent to the leading tip 86 of the tool's plunger 59, and the first end 20 of suture anchor 5 is located close to but outside of the tool's front surface 62. It is to be appreciated that as the suture anchor is forced into the interior bore 68 of tool 53 in the aforementioned manner, the relative sizing of the suture anchor and the tool's bore 68 will cause the normally-curved barb 15 to be bent back so that it extends substantially parallel to the length of the coupling member 10, which itself forms a close sliding fit with the walls of bore 68. Suture anchor 5 is loaded into tool 53 so that the coupling member's side slot 35 is aligned with the sheath's side slot 71; however, the suture anchor is left so that its first end 20 is sufficiently far outside of sheath 56 so that substantially all of the anchor's blind hole 30 remains outside of sheath 56. Still looking at FIG. 4A, a suture 89 is attached to suture anchor 5 while the suture anchor is held in the tip of installation tool 53 so as to form the complete suture and suture anchor assembly. Suture 89 is a conventional suture comprising a first end 92 and an opposite second end 95. Preferably suture 89 is made out of a polyester fiber and has a diameter of approximately 0.020 inches. A needle (not shown) may or may not be attached to the suture's second end 95. Suture 89 is attached to suture anchor 5 by tying a knot 97 about the first end 92 of suture 89, slipping the knotted end of the suture into the coupling member's blind hole 30 and threading the body of the suture into the coupling member's side slot 35, and then pulling the second end 95 of the suture taut so that knot 97 is captured inside the suture anchor's blind hole 30 while the suture extends out through the anchor's slot 35. Once suture 89 has been attached to suture anchor 5 in the foregoing manner so as to form the complete suture and suture anchor assembly, the suture and suture anchor assembly may then be pushed further into installation tool 53 so that the coupling member's first end 20 is positioned substantially flush with the installation tool's front surface 62 and the body of the suture extends out through the installation tool's side slot 71, as shown in FIG. 4B. Either before or after the suture anchor has been loaded into the installation tool and the suture attached to the suture anchor so as to form the complete suture and suture anchor assembly, but in any case before the suture and suture anchor assembly is deployed into bone, an appropriate hole must be formed in the bone which is to receive the suture and suture anchor assembly. Looking next at FIG. 5, a hole 98 is drilled into the bone 99 which is to receive the suture and suture anchor assembly. Hole 98 preferably has a diameter of approximately 0.116 inches and a depth of approximately 1.25 inches. Hole 98 is formed with conventional tools of the sort well known in the art.

Figure 6:
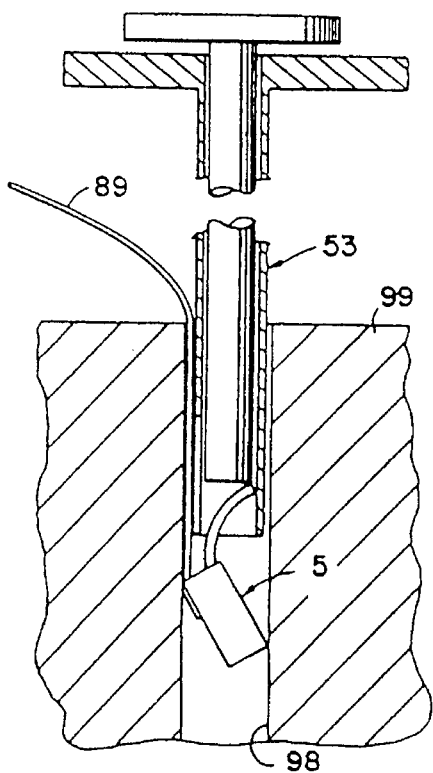
FIG. 6 is a side view in elevation, partially in section, showing a suture and suture anchor assembly and an installation tool, with the installation tool having been inserted into a hole formed in a bone and the suture and suture anchor assembly in the process of being ejected out of the installation tool and into the hole formed in the bone.
Figure 7:
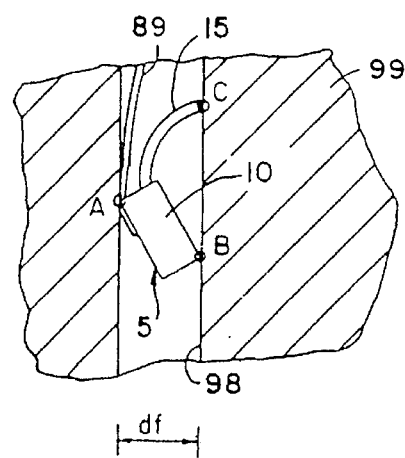
FIG. 7 is a side view in elevation, partly in section, showing a suture and suture anchor assembly after it has been deployed into a bone.

After suture anchor 5 has been loaded into installation tool 53 and suture 89 attached to the suture anchor so as to form the complete suture and suture anchor assembly, in the manner shown in FIGS. 4A and 4B, and after the hole 98 has been formed in bone 99, the suture anchor (and its attached first end of the suture) is ready to be set into bone 99. This is achieved by inserting the leading end of installation tool 53 into hole 98, with the free end of suture 89 passing out through the installation tool's side slot 71 and along the wall of hole 98 to the region outside the bone. When the installation tool has been inserted to the proper depth, i.e., approximately 0.75 inches, the installation tool's plunger 59 is driven forward until the plunger's head section 83 engages the sheath's end surface 65, thereby ejecting suture anchor 5 out of the installation tool and into hole 98 formed in bone 99, in the manner shown in FIG. 6. It is to be appreciated that as the suture anchor' coupling member 10 leaves the tool and the suture anchor's barb 15 approaches the mouth of tool bore 68, the length of barb 15 is progressively released from the confines of the deployment tool's bore 68, thereby allowing the barb to spring back to its normally curved, unstressed position. This progressive restoration of the barb's curved state causes the suture anchor to pivot on itself as it leaves the tool, so that the suture anchor swings itself off-center and engages bone 99 at three different contact points A, B and C (see FIG. 7), thereby securely lodging itself in bone hole 98. The free second end 95 of suture 89 is then available to fasten objects to bone 99, in ways well known in the art.

It is to be appreciated that suture anchor 5 and bone hole 98 must be properly dimensioned relative to one another if the suture anchor is to properly and securely lodge itself in the hole formed in the bone. In particular, it has been found that if the diameter of the unconstrained suture anchor is initially "di" (when measured in the manner shown in FIG. 1), and if the diameter of the suture anchor when loaded into the installation tool is subsequently "dt" (when measured in the manner sown in FIG. 4B), and if the diameter of the hole 98 in bone 99 is "df" (when measured in the manner shown in FIG. 7), then in order for the present design to work properly, the dimension di must be at least as great as the dimension df, and the dimension df must be much greater than the dimension dt, i.e., $di \geq df \gg dt$.

One consequence of the foregoing relationship is that it requires that the barb 15 be formed out of a material which is simultaneously capable of both (a) substantial resiliency, since the barb must be capable of being bent from a substantially 90 degree arc to a substantially straight length when disposed within the deployment tool, and (b) substantial strength, since barb 15 must be capable of holding the suture anchor securely in place despite the application of fairly strong forces to the free end 95 of suture 89. These simultaneous requirements of high elasticity and high strength are achieved by forming the barb 15 out of the aforementioned nickel titanium alloy or an equivalent non-nickel titanium material.

Looking next at FIG. 8 and 9, there is shown another suture anchor 105 which generally comprises a coupling member 110 and a barb 115.

Coupling member 110 comprises a piece of 6Al4V titanium alloy having a first end 120 and a second end 125. Coupling member 110 has a bore 127 opening on its second end 125 and a counterbore 130 opening on its first end 120. Bore 127 and counterbore 130 intersect one another at an annular shoulder 132. A side slot 135 opens on the coupling member's first end 120 and communicates with both bore 127 and counterbore 130. Side slot 135 terminates in an included surface 140 intermediate the length of coupling member 110. Coupling member 110 has a length of approximately 0.156 inches and a width of approximately 0.062 inches, bore 127 has a width of approximately 0.031 inches, counterbore 130 has a width of approximately 0.042 inches, shoulder 132 is set approximately 0.050 inches from first end 120, and side slot 135 has a length of approximately 0.093 inches (as measured between first end 120 and the point where inclined surface 140 opens on the exterior of coupling member 110) and a width of approximately 0.020 inches.

Barb 115 comprises a curved length of nickel titanium alloy having a first end 145 and a second end 150. Barb 115 has a width of approximately 0.026 inches and, in its unrestrained state, comprises an arc of approximately 135 degrees of a loop approximately 0.250 inches in diameter (when measured to the inside edge of the loop). Barb 115 is attached to the coupling member's second end 125 by press fitting the barb's first end 145 into bore 127, whereby the barb's second end 150 extends upward away from the coupling member. Coupling member 110 may or may not also be crimped inward as shown at 152 to help maintain barb 115 in bore 127. Barb 115 is capable of being elastically deformed to a substantially straight length when desired (e.g. so that the barb's second end 150 is aligned with its first end 145, as well as with the coupling member's first end 120 and its second end 125).

A conventional suture 89 is attached to suture anchor 105 in precisely the same manner that suture 89 is attached to suture anchor 5, i.e., by capturing a knotted end of the suture in the suture anchor's counterbore 130 while the suture anchor is held in the tip of the installation tool, and suture anchor 105 and its attached suture are thereafter used in precisely the same manner as the aforementioned suture and suture anchor assembly incorporating suture anchor 5.

It is also anticipated that one might attach the suture to the suture anchor prior to loading the suture anchor into the installation tool. This could be accomplished using the aforementioned suture anchors 5 and 105 or, more preferably, this is done using a slightly different suture and suture anchor assembly.

Looking next at FIG. 10, there is shown a suture and suture anchor assembly 201 which comprises a suture 202 which is attached to a suture anchor 205. Suture anchor 205 comprises a coupling member 210 and a barb 215.

Suture 202 comprises a conventional suture comprising a first end 203 and an opposite second end 204. Preferably suture 202 is made out of a polyester fiber and has a diameter of approximately 0.020 inches. A needle (not shown) may or may not be attached to the suture's second end 204.

Coupling member 210 comprises a piece of hypodermic tubing having a first end 220 and a second end 225. Coupling member 210 has a center bore 227 passing therethrough. Coupling member 210 is preferably formed out of 316 L stainless steel and has a length of approximately 0.156 inches, an outer diameter of approximately 0.068 inches and an inner diameter of approximately 0.043 inches.

Barb 215 comprises a piece of nickel titanium alloy wire which is normally curved in its unrestrained state. Barb 215 has a first end 245 and a second end 250 and is approximately 0.026 inches in diameter. In its unrestrained state, barb 215 comprises an arc of approximately 120 degrees of a loop approximately 0.282 inches in diameter (when measured to the inside edge of the wire). Barb 215 is capable of being elastically deformed to a substantially straight length when desired, yet will spring back to its original curved form immediately upon release.

Suture and suture anchor assembly 201 is assembled by passing coupling member 210 over suture 202 so that the coupling member's first end 220 is disposed near the suture's first end 203. Then suture 202 is knotted on itself at 251 adjacent its first end 203 so that coupling member 210 is prevented from sliding off the first end of the suture. Next, coupling member 210 is pushed towards the suture's knot 251 until the coupling member's first end 220 engages (or nearly engages) the suture's knot. Once this has been done, barb 215 is inserted, first end 245 leading, into the second end 225 of coupling member 210. This results in the barb's second end 250 extending at approximately a right angle to the length of coupling member 210. Coupling member 210 is then crimped inward at 252 so as to fix suture 202 and barb 215 to coupling member 210. On account of the foregoing construction, it will be appreciated that suture 202, coupling member 210 and barb 215 are all securely fixed in position relative to one another when the suture and suture anchor assembly 201 is properly assembled.

Suture and suture assembly 201 is intended to be preassembled outside the operating room. When suture and suture anchor assembly 201 is thereafter to be used, it simply needs to be loaded into the front end of installation tool 53 in the manner previously described for suture anchors 5 and 105, except that inasmuch as suture 202 is already attached to suture anchor 205, the step of attaching the suture to the suture anchor while the suture anchor is supported in the front end of the installation tool may be omitted. Suture and suture anchor assembly 201 is then utilized the same manner as the suture and suture anchor assemblies previously described.

FURTHER MODIFICATIONS OF THE INVENTION

It is, of course, possible to modify the various embodiments just described without departing from the scope of the present invention.

Thus, for example, the precise dimensions of sutures 89 and 202, coupling members 10, 110 and 210, barbs 15, 115 and 215, tool 53, and bone hole 98 could all be varied from the preferred dimensions described above, so long as the fundamental relationships of the dimensions are not changed so dramatically as to render the present invention unworkable. Of course, it should be appreciated that the fundamental relationship of $di \geq df >> dt$ described above cannot be voided.

Figure 11:
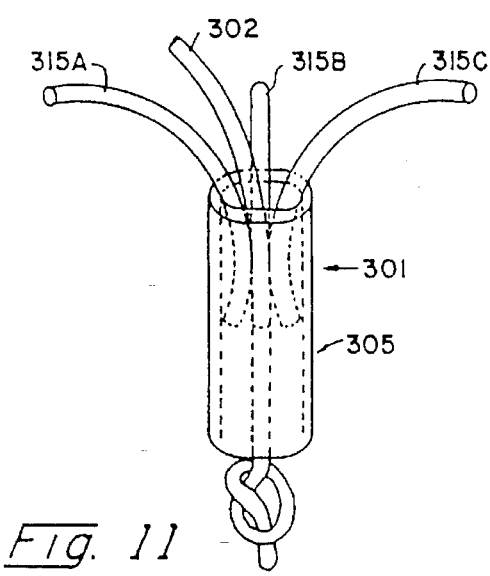
FIG. 11 is a perspective view showing another suture and suture anchor assembly formed in accordance with the present invention.
Figure 12:
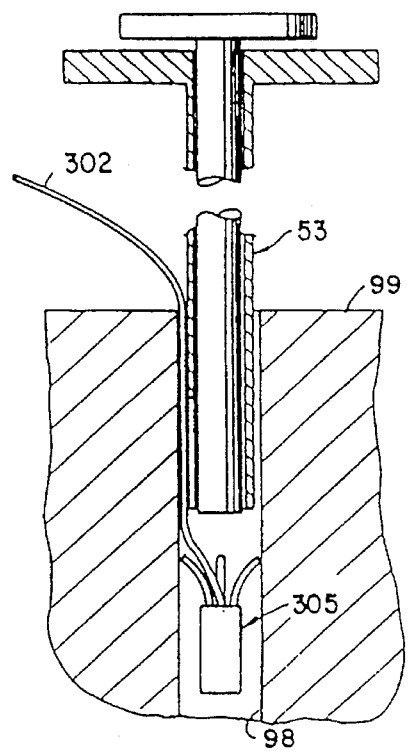
FIG. 12 is a side view in elevation, partly in section, showing the suture and suture anchor assembly of FIG. 11 immediately after it has been ejected out of an installation tool and into a hole formed in a bone.

It is possible to vary the number of barbs provided on the suture anchors. More particularly, two, three or even more barbs might be provided on the suture anchors. By way of example, a suture and suture anchor assembly 301 comprising a suture 302 and a suture anchor 305 having three barbs 315A, 315B and 315C is shown in FIG. 11. Barbs 315A, 315B and 315C are all identical to the aforementioned barb 215 of suture anchor 205, and are preferably equally spaced about the perimeter of the coupling member. It is to be appreciated that the use of multiple, equally-spaced barbs on the suture anchor may eliminate the tendency of the suture anchor to pivot off-center as it is ejected from the installation tool during deployment of the suture anchor, as happens with a suture anchor comprising only a single barb (see FIG. 6 and 7); the multi-barbed suture anchor may not tend to pivot off-center as it is ejected from the installation tool, since all of the suture anchor's barbs will tend to leave the installation tool and spring back to their curved, unrestrained shape substantially simultaneously with one another. In this respect, FIG. 12 illustrates the three barb suture anchor 305 being ejected from the installation tool 53 without the pivoting action of the single barb suture anchor, so that the suture anchor 305 is set in bone hole 98 so that the longitudinal axis of the suture anchor is substantially aligned with the central axis of bone hole 98; FIG. 12 may be compared with FIGS. 6 and 7, which illustrate the manner in which a single barb suture anchor sets itself into bone. It will be appreciated that suture anchor 305 is deployed in substantially the same manner as suture anchor 205.

Figure 13:
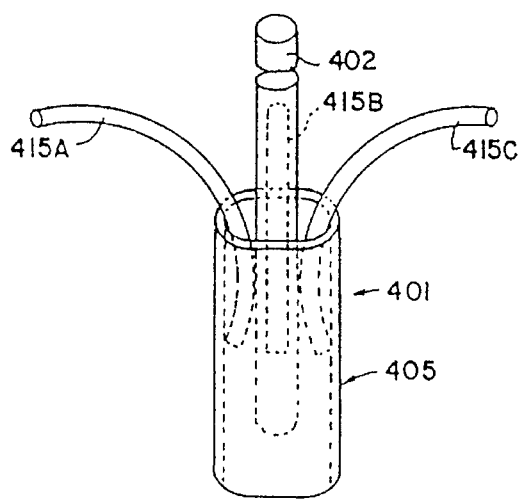
FIG. 13 is a perspective view showing a post and post anchor assembly formed in accordance with the present invention.
Figure 14:
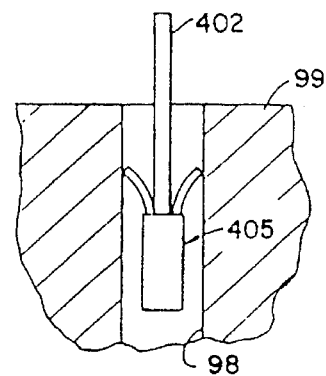
FIG. 14 is a side view in elevation, partly in section, showing the post and post anchor assembly of FIG. 13 immediately after it has been ejected out of an installation tool and into a hole formed in a bone.

It is also possible to replace the suture 302 of the suture anchor 305 with a straight post which may be used to attach prostheses to bone. FIG. 13 illustrates a post and post anchor assembly 401 comprising a post 402 and a post anchor 405 having three barbs 415A, 415B and 415C. FIG. 14 illustrates post and post anchor assembly 401 set in bone 99. It is to be appreciated that inasmuch as it is generally desirable to set post anchor 405 so that post 402 extends substantially parallel to the axis of bone hole 98, anchors equipped with a post 402 will preferably be formed with multiple, equally-spaced barbs. It will be appreciated that post and post anchor assembly 401 is deployed in substantially the same manner as suture and suture anchor assembly 301.

Figure 15:
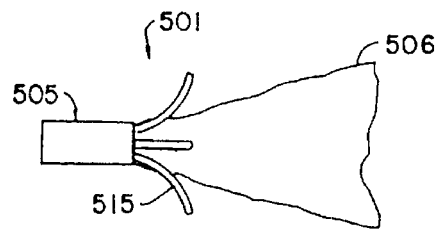
FIG. 15 is a partial side view in elevation showing a prosthesis and prosthesis anchor assembly formed in accordance with the present invention.

It is also possible to fasten prosthetic devices directly to the anchor's coupling member and omit the use of sutures or posts altogether. In this respect, FIG. 15 illustrates a prosthesis and prosthesis anchor assembly 501 which comprises a prosthesis anchor 505 which is attached to one end of a prosthesis 506. Prosthesis 506 is attached to anchor 505 having barbs 515 and in substantially the same manner that suture 302 is attached to suture anchor 305 and post 402 is attached to post anchor 405, i.e., by inserting a portion of the prosthesis into the interior of the coupling member and then crimping the coupling member about the encompassed portion of the prosthesis to capture it in place. Prosthesis and prosthesis anchor assembly 501 is deployed in substantially the same manner that post and post anchor assembly 401 is deployed.

It is also possible to use a material other than a nickel titanium alloy to form the barbs 15, 115, 215, 315, 415 and 515, as discussed above.

Figure 16:
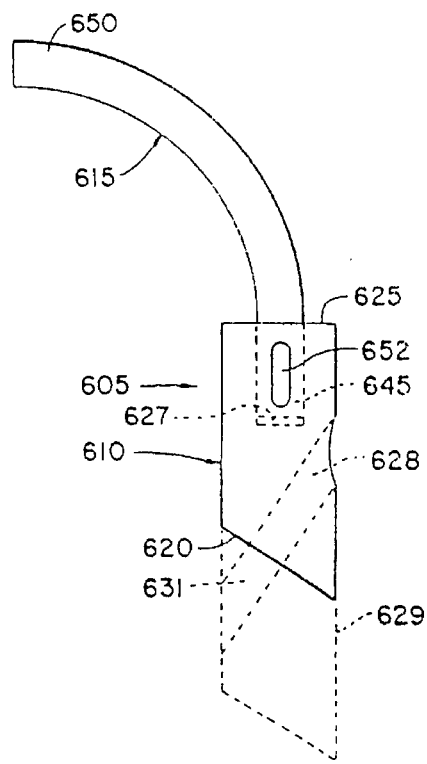
FIG. 16 is a side view in elevation showing another suture anchor formed in accordance with the present invention.

Looking next at FIG. 16, there is shown a suture anchor 605 which constitutes still another embodiment of the invention. Suture anchor 605 comprises a coupling member 610 and a barb 615.

Coupling member 610 comprises a piece of 6A14V titanium alloy having a first end surface 620 and a second end surface 625. The first end surface 620 is disposed at an angle of approximately 30 degrees to the coupling member's longitudinal axis, and the second end surface 625 is disposed at a right angle to the coupling member's longitudinal axis, as shown. Coupling member 610 has a blind hole 627 opening on the second end surface 625, and a bore 628 extending at an angle between the coupling member's side wall and bottom end surface 620, as shown. Coupling member 610 has a length of approximately 0.160 inches and a diameter of approximately 0.053 inches, blind hole 627 has a depth of approximately 0.070 inches and a diameter of approximately 0.028 inches, and bore 628 has a diameter of approximately 0.028 inches.

Barb 615 comprises a curved length of nickel titanium alloy having a first end 645 and a second end 650. Barb 615 has a diameter of approximately 0.026 inches and, in its unrestrained state, comprises an arc of approximately 135 degrees of a loop approximately 0.250 inches in diameter (when measured to the inside of the loop). Barb 615 is attached to the coupling member by press fitting the barb's first end 645 into the coupling member's blind hole 627, whereby the barb's second end 650 extends upward away from the coupling member. Coupling member 610 may or may not also be crimped inward at one or more points as shown at 652 to help lock it to barb 615. Barb 615 is capable of being elastically deformed to a substantially straight length when desired (e.g. so that the barb's second end 650 is aligned with its first end 645, as well as with the opposite ends of the coupling member).

Figure 17:
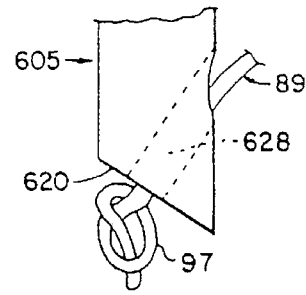
FIG. 17 is a side view in elevation showing the base of the suture anchor shown in FIG. 16 attached to a suture by a single overhand knot.

Looking next at FIG. 17, a conventional suture 89 is attached to suture anchor 605 by threading the suture through bore 628 while the suture anchor is held in the tip of the installation tool 53 (not shown in FIG. 17), and then tying a knot 97 in the end of the suture adjacent the suture anchor's first end 620 and pulling the free end of the suture taut so that the knot is drawn up tight against the suture anchor's first end surface 620. Suture anchor 605 and its attached suture are thereafter utilized in precisely the same manner as the aforementioned suture and suture anchor assembly incorporating suture anchor 5.

Figure 18:
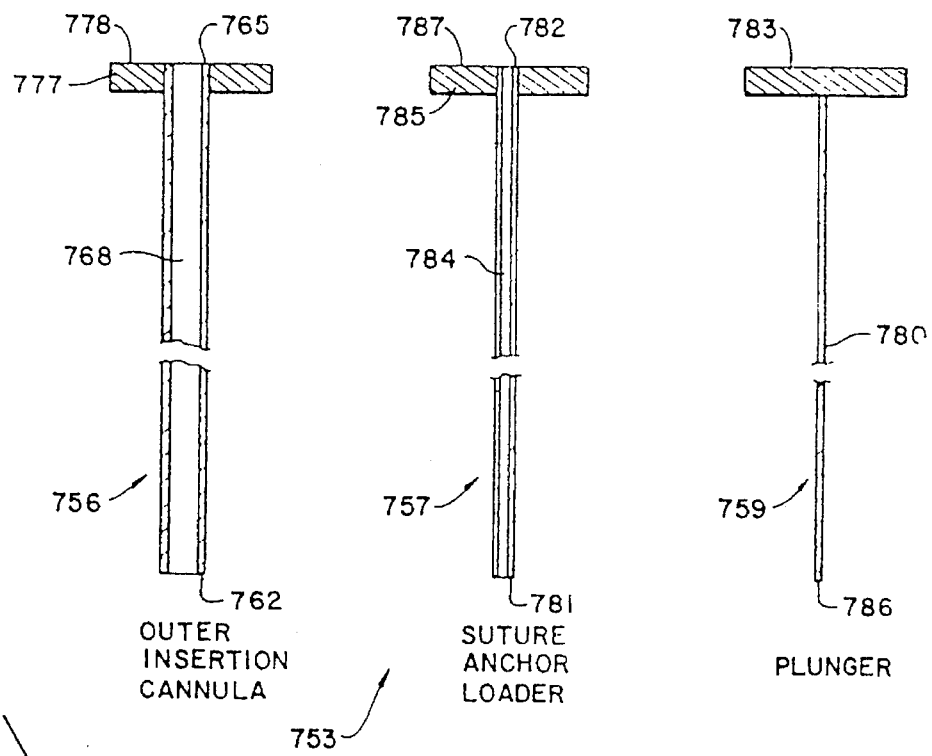
FIG. 18 is a side view in elevation, in section, showing three coaxial members which together comprise an alternative installation tool which can be used to insert the suture anchors of FIGS. 1, 8 or 16 into bone.

Looking next at FIG. 18, there is shown an alternative installation tool 753 which may be used to deploy any of the suture anchors and suture anchor assemblies previously described (for purposes of illustration only, installation tool 753 will hereinafter be discussed in the context of the suture anchor 605 of FIGS. 16 and 17). Installation tool 753 comprises a hollow sheath or cannula 756, a hollow loader or inserter 757 and a solid plunger 759.

Hollow sheath 756 terminates in a flat annular surface 762 at its front end and a flat annular surface 765 at its rear end. Surfaces 762 and 765 are disposed at an angle substantially perpendicular to the longitudinal axis of sheath 756. Sheath 756 has an axial bore 768 extending between its front and rear surfaces 762 and 765. Sheath 756 includes a disk-like finger grip 777 which is affixed to the rear end of the outer sheath member and includes a flat surface 778 which is coplanar with the sheath member's rear surface 765. Sheath 756 preferably has an outer diameter (i.e., forward of finger grip 777) of approximately 0.095 inches, an inner diameter of approximately 0.071 inches, and a length of approximately 4.0 inches.

Hollow loader 757 terminates in a flat annular surface 781 at its front end and a flat annular surface 782 at its rear end. Surfaces 781 and 782 are disposed at an angle substantially perpendicular to the longitudinal axis of sheath 757. Loader 757 has an axial bore 784 extending between its front surface 781 and its rear surface 782. Loader 757 includes a disk-like finger grip 785 which is attached to the rear end of the loader member and includes a flat surface 787 that is coplanar with the loader's rear surface 782. Loader 757 preferably has an outer diameter (i.e., forward of finger grip 785) of approximately 0.065 inches, an inner diameter of approximately 0.047 inches, and a length of approximately 4.13 inches. Loader 757 is sized so that it will make a close sliding fit within bore 768 of sheath 756, as will hereinafter be described in further detail, and also so that its leading tip 781 will not protrude from the front end of the sheath member 756 when the loader is inserted into the axial bore 768 and the loader's finger grip 785 is in engagement with the sheath's rear surface 765, as will hereinafter be described in further detail.

Plunger 759 includes a solid body section 780 and a head section 783. Body section 780 has a round cross-section and terminates in a front surface 786. Plunger 759 is sized so that its body section 780 will make a close sliding fit within bore 784 of loader 757 and also so that its leading tip will protrude from the front end of the loader member a short distance when the plunger's head section 783 is in engagement with the loader member's rear surface 782, as will hereinafter be described in further detail. Plunger 759 preferably has a diameter of approximately 0.047 inches forward of head section 783, and a length of approximately 4.32 inches, as will hereinafter be described in further detail.

Figure 19:
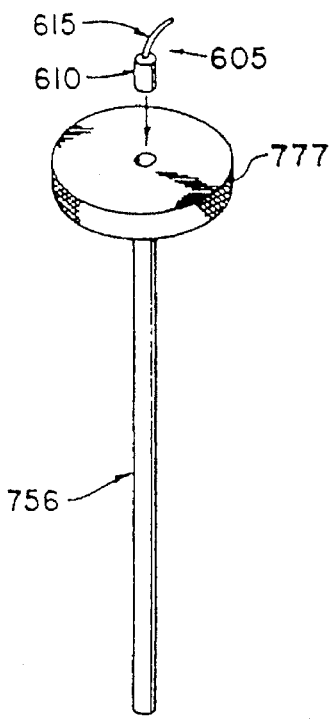
FIG. 19 is a perspective view showing a suture anchor being loaded into the top end of the outer insertion cannula shown in FIG. 18.
Figure 20:
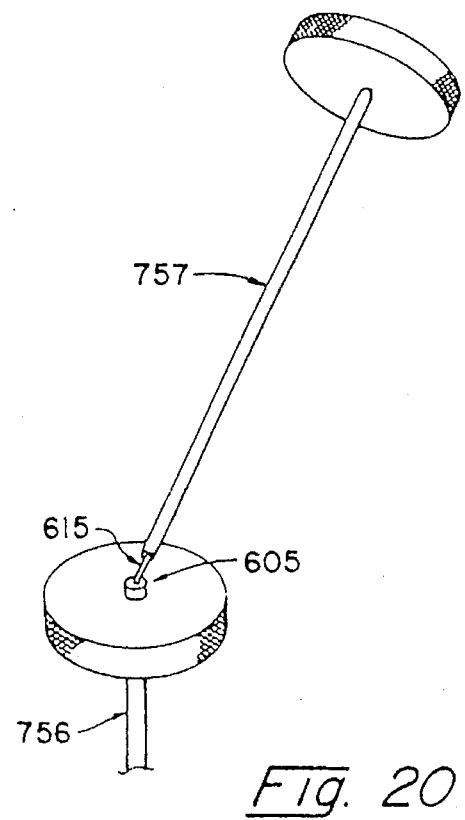
FIG. 20 is a perspective view showing the suture anchor loader shown in FIG. 18 being used to straighten out the suture anchor barb in order to install the suture anchor into the outer insertion cannula.
Figure 20A:
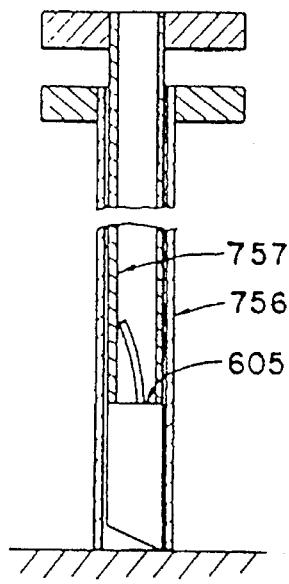
FIG. 20A is a side view, partially in section, showing the suture anchor loader and suture anchor installed within the outer insertion cannula, wherein the insertion cannula is rested against a flat surface and the suture anchor loader is bottomed against the suture anchor to assure the proper dimensional relationship between the loader, insertion cannula and suture anchor.
Figure 21:
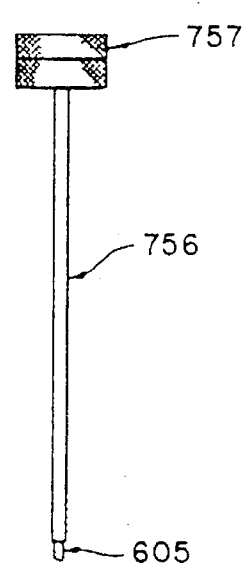
FIG. 21 is a side view in elevation of the subassembly shown in FIG. 20, comprising the suture anchor, the outer insertion cannula and the suture anchor loader.
Figure 22A:
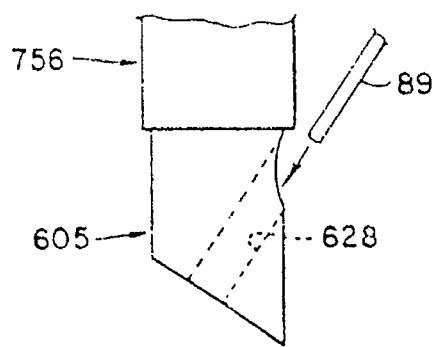
FIG. 22A is a side view in elevation showing the tip of the cannula subassembly shown in FIG. 21, having a suture being loaded into the suture retention hole.
Figure 22B:
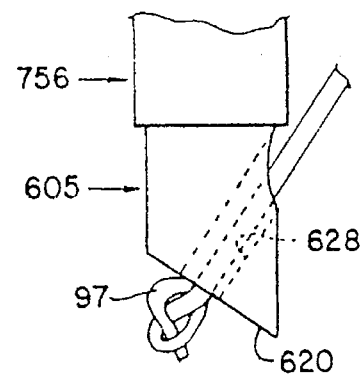
FIG. 22B is a side view in elevation showing the tip of the cannula subassembly shown in FIG. 21 after the suture has been loaded into the suture retention hole and tied with an overhand knot.
Figure 23:
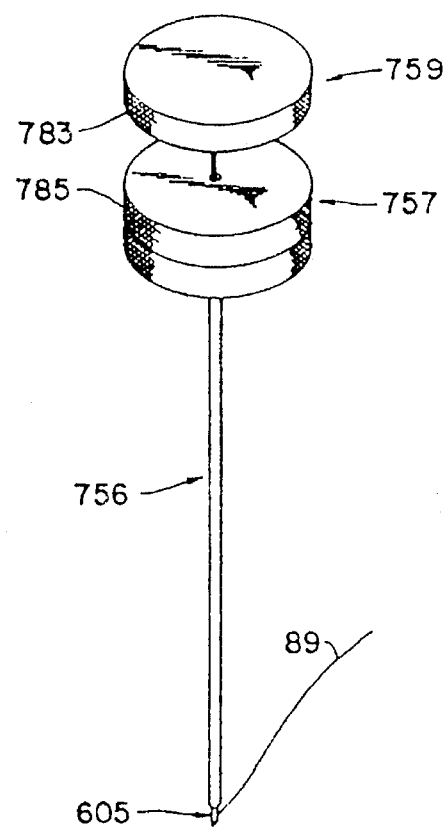
FIG. 23 is a perspective view showing the plunger of FIG. 18 inserted into the suture anchor subassembly shown in FIG. 22B, prior to release of the suture anchor.
Figure 24:
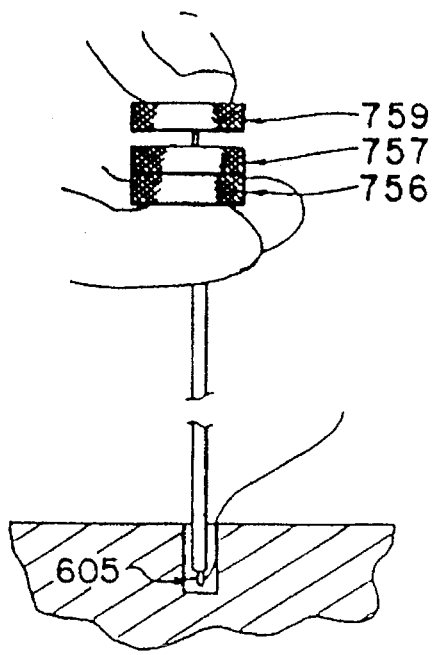
FIG. 24 is a side view showing the suture anchor with attached suture inserted into a predrilled hole, prior to the release of the suture anchor by the insertion tool.
Figure 25:
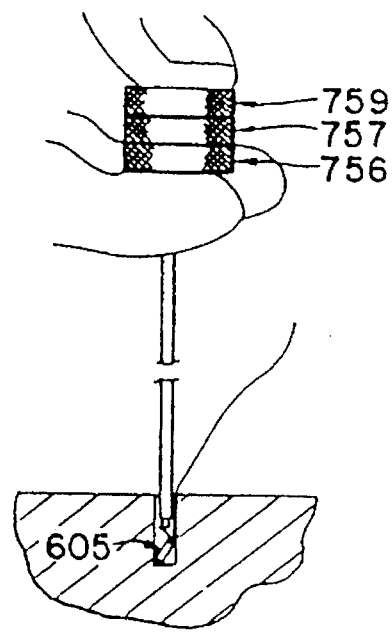
FIG. 25 is a side view showing the suture anchor with attached suture inserted into the predrilled bone hole and released from the insertion tool by bottoming the tool's plunger element.

Installation tool 753 is intended to be utilized as follows. Looking first at FIG. 19, suture anchor 605 is loaded into the top end of sheath member 756 so that the suture anchor's coupling member 610 resides in axial bore 768 and the anchor's barb 615 extends beyond finger grip 777 of the sheath member. Looking next at FIG. 20, the front end 781 of loader 757 is then slipped over the free end of the suture anchor's barb 615 so that the free end of the barb extends within the loader member's axial bore 784. Then loader member 757 is (a) forced into coaxial alignment with outer sheath member 756, thereby straightening out barb 615 in the process, and (b) pushed into the interior of sheath member 756, carrying the suture anchor downward within the sheath member as it goes. In order to assure the barb 615 of suture anchor 605 is completely contained within inserter 757 such that suture anchor loader surface 781 contacts suture anchor surface 625, it is necessary (FIG. 20A) to rest insertion cannula surface 762 against a stationary surface 790 while bringing suture anchor loader 757 downward into direct contact with suture anchor surface 625. Sheath member 756 and loader member 757 are carefully sized relative to one another (and suture anchor 605) so that when the loader member's finger grip 785 is in contact with the sheath member's top surface 765, the suture anchor will protrude slightly from the bottom end of the sheath member, as shown in FIG. 21. More specifically, as seen in FIGS. 22A and 22B, sheath member 756 and loader member 757 are sized relative to one another (and suture anchor 605) so that both ends of the suture anchor's diagonal bore 628 will be exposed to view when the loader member's finger grip 785 is in contact with the sheath member's top surface 765. With the suture anchor so held by the installation tool, a conventional suture 89 may then be easily attached to the suture anchor by passing the suture through the anchor's diagonal bore 628 and tying a knot 97 at the end of the suture which can bear against the bottom end 620 of the coupling member, as shown in FIGS. 22A and 22B. Once this has been done, plunger member 759 may be inserted into the loader member's internal bore 784 (FIG. 23) and pressed downward until its bottom tip 786 contacts the suture anchor barb contained in the loader member's bore 784. By appropriately sizing the respective members involved, the head section 783 of the plunger member will remain slightly above finger grip 785 of loader member 757 when the plunger member's tip 786 engages suture anchor 605. Thereafter, when the installation tool is to deploy the fastener into bone, the tip of the installation tool is inserted into a hole formed in the bone, and then head section 783 of plunger member 759 is forced downward into contact with finger grip 785 of loader member 757, thereby ejecting the suture anchor out of the installation tool and into the bone, as shown in FIGS. 24 and 25.

Another possible modification is to extend the length of the coupling member 610 (FIG. 16) beyond the hole 628, as shown in dotted lines at 629, whereby the hole 628 will be formed so as to extend transversely across the coupling member, as shown as 631. Such an arrangement has the advantage that in soft bone a pulling force on the suture 89 may cause the coupling member to rotate, e.g. as much as 90 degrees, so as to assure a firm and stable anchor.

Still other changes will be obvious to persons skilled in the art and are believed to fall within the scope of the present invention.

ADVANTAGES OF THE INVENTION

Numerous advantages are obtained by employing the present invention.

More specifically, improved apparatus is provided for attaching objects to bone which avoids the aforementioned problems associated with prior art devices.

In addition, a suture anchor is provided for anchoring one end of a piece of conventional suture in bone and leaving the other end of the piece of suture residing free outside the bone so that the free end of the suture can then be used to attach the desired object (e.g. a ligament or prosthesis) to the bone.

Furthermore, a suture anchor is provided for anchoring one end of a piece of conventional suture in bone which is made out of biocompatible material which eliminate, or at least minimize, any problem of rejection by surrounding tissue.

Also, a suture anchor is provided for anchoring one end of a piece of conventional suture in bone which will attach itself securely to the target bone and which has virtually no tendency to migrate from its deployment site.

Furthermore, a suture anchor is provided for anchoring one end of a piece of conventional suture in bone which is low in cost, simple to manufacture, and reliable in use.

In addition, a novel method is provided for attaching objects to bone which utilizes the novel suture anchor now disclosed.

And a novel suture and suture anchor assembly comprising a suture and suture anchor is provided for anchoring one end of a piece of suture in bone and leaving the other end of the suture residing free outside the bone so that the free end of the suture can then be used to attach the desired objects (e.g. a ligament or prosthesis) to the bone.

Yet another object of the present invention is to provide a novel method for attaching objects to bone which utilizes the novel suture and suture anchor assembly now disclosed.

In addition, a novel post and post anchor assembly comprising a post and post anchor is provided for anchoring one end of a post in bone and leaving the other end of the post residing free outside the bone so that the free end of the post can be used to attach objects to the bone.

Also, a novel method is provided for attaching objects to bone which utilizes the novel post and post anchor assembly now disclosed.

And a novel prosthesis and prosthesis anchor assembly comprising a prosthesis and a prosthesis anchor is disclosed for anchoring one end of the prosthesis in bone.

Also, a novel method is provided for attaching prosthesis to bone which utilizes the novel prosthesis and prosthesis anchor assembly now disclosed.

And a novel installation tool for deploying the novel suture anchor in bone is disclosed.

Still other advantages of the present invention will be obvious to persons skilled in the art.

What we claim is:

1. Apparatus for attaching a first object to a second object, said apparatus comprising:

a body having a longitudinal axis and a maximum cross-section perpendicular to said longitudinal axis, said body being adapted for longitudinal insertion into said second object;

attachment means disposed on said body for attaching said first object to said apparatus; and retaining means for resisting forces tending to withdraw said apparatus from said second object after its insertion therein, said retaining means comprising at least one flexible element having first and second portions, said first portion being supported by said body and said second portion normally extending outboard from said body so that said second portion is located outwardly of a longitudinal axial projection of said maximum cross-section of said body, said flexible element being substantially elastically deformable such that said second portion of said flexible element is capable of being located substantially within a longitudinal axial projection of said maximum cross-section of said body.

2. The apparatus in accordance with claim 1 wherein said retaining means comprises a barb of nickel titanium alloy.

3. The apparatus in accordance with claim 1 wherein said retaining means second portion is curved when said second portion extends outwardly of said longitudinal projection of said maximum cross-section of said body.

4. The apparatus in accordance with claim 1 wherein said attachment means comprises an opening in said body for receiving a suture, and a slot in a side of said body extending from said opening to permit passage of said suture therethrough.

* * * * *